United States Patent
Kyllonen et al.

(10) Patent No.: US 10,398,873 B1
(45) Date of Patent: Sep. 3, 2019

(54) ROLLED SUBSTRATE CABLE (71) Applicant: AUTOMATED ASSEMBLY CORPORATION, Lakeville, MN (US)

(72) Inventors: Kimmo Kyllonen, Shakopee, MN (US); David Neuman, Randolph, MN (US); Scott Lindblad, Chaska, MN (US)

(73) Assignee: Automated Assembly Corporation, Lakeville, MN (US)

( * ) Notice: Subject to any disclaimer, the term of this patent is extended or adjusted under 35 U.S.C. 154(b) by 0 days.

(21) Appl. No.: 16/041,392

(22) Filed: Jul. 20, 2018

(51) Int. Cl.
*A61M 25/00* (2006.01)
*H01F 7/06* (2006.01)
*H02G 3/04* (2006.01)

(52) U.S. Cl.
CPC ...... *A61M 25/005* (2013.01); *A61M 25/0054* (2013.01)

(58) Field of Classification Search
CPC .............. A61M 25/00; A61M 25/005; A61M 25/0054; H01F 7/06; H02G 3/04; H05K 1/028; H05K 3/107; H05K 2201/051; H05K 2201/09827; Y10T 29/49071
USPC ................................................ 174/255, 72 A
See application file for complete search history.

(56) References Cited

U.S. PATENT DOCUMENTS

| | | | |
|---|---|---|---|
| 5,222,178 A * | 6/1993 | Betker | G02B 6/4407 385/110 |
| 5,445,155 A | 8/1995 | Sieben | |
| 5,502,287 A * | 3/1996 | Nguyen | H01B 7/0838 156/53 |
| 6,140,146 A | 10/2000 | Brady et al. | |
| 6,259,408 B1 | 7/2001 | Brady et al. | |
| 6,478,229 B1 | 11/2002 | Epstein | |
| 6,951,596 B2 | 10/2005 | Green et al. | |
| 6,986,826 B2 | 1/2006 | Dronzek, Jr. | |
| 7,102,520 B2 | 9/2006 | Liu et al. | |
| 7,240,873 B2 | 7/2007 | Eikmeier et al. | |
| 7,868,766 B2 | 1/2011 | Gengel et al. | |
| 7,901,533 B2 | 3/2011 | Steidinger | |
| 7,922,094 B2 | 4/2011 | Banerjee et al. | |
| 8,430,324 B2 | 4/2013 | Baba et al. | |
| 8,448,871 B2 | 5/2013 | Hioki | |
| 8,728,053 B2 | 5/2014 | Broaddus et al. | |
| 9,833,608 B2 | 12/2017 | Masson | |
| 9,844,643 B2 | 12/2017 | Beasley et al. | |
| 2002/0155243 A1 | 10/2002 | Kobe et al. | |
| 2003/0136503 A1 | 7/2003 | Green et al. | |
| 2008/0007409 A1 | 1/2008 | Ferry et al. | |
| 2008/0055044 A1 | 3/2008 | Fronek et al. | |
| 2008/0088448 A1 | 4/2008 | Steidinger | |
| 2008/0314626 A1 * | 12/2008 | Moore | G06F 3/0412 174/255 |
| 2009/0258787 A1 * | 10/2009 | Wilkie | H01L 39/141 505/231 |

(Continued)

FOREIGN PATENT DOCUMENTS

WO          2007000407 A2      1/2007

*Primary Examiner* — Timothy J Thompson
*Assistant Examiner* — Guillermo J Egoavil
(74) *Attorney, Agent, or Firm* — Crawford Maunu PLLC (57) ABSTRACT

A disclosed cable includes a roll of flexible substrate. The substrate has opposing first and second surfaces and the roll is structured around an axis. A plurality of electrically conductive wires are attached to the first surface of the substrate, and the roll of flexible substrate and attached plurality of wires have alternating layers of wires and substrate.

47 Claims, 5 Drawing Sheets

(56) References Cited

U.S. PATENT DOCUMENTS

| | | |
|---|---|---|
| 2010/0001862 A1 | 1/2010 | Wilson et al. |
| 2011/0088945 A1* | 4/2011 | Yanagimoto ............ H05K 1/028 174/72 A |
| 2011/0101107 A1 | 5/2011 | Kessler |
| 2011/0114734 A1 | 5/2011 | Tiedmann et al. |
| 2011/0241834 A1 | 10/2011 | McAllister et al. |
| 2013/0099003 A1 | 4/2013 | Tarantino et al. |
| 2014/0121557 A1 | 5/2014 | Gannon et al. |

* cited by examiner

FIG. 14

ROLLED SUBSTRATE CABLE

FIELD OF THE INVENTION

The disclosure describes a rolled substrate having parallel wires disposed on a surface of the substrate.

BACKGROUND

Intravascular catheters can be used for medical diagnoses and interventions. Some intravascular catheters include a tube having conductors that can be used to stimulate internal organs and/or carry return signals for analysis.

Catheter makers face challenges in making catheters that are both economically competitive and functional. For many applications, conductors are formed on a flexible substrate. Patterns of conductors can be formed on the substrate using a print-and-etch process, which can be prohibitively expensive. The expense is attributable in part to the print-and-etch processes used in creating the wiring pattern. Expensive chemicals or lasers may be used for print-and-etch processes, and hazardous waste may be a byproduct.

In addition to being costly and environmentally unfriendly, reliability and durability are challenges presented by printed-and-etched catheters. With lengths of many catheters in the range of 2 meters, catheter makers may experience low yields in forming conductive patterns on a long narrow substrate. In addition, crosstalk problems may appear in the resulting structure, and normal usage involving bending and twisting of the catheter may damage the conductors, which reduces the product life expectancy and increases costs.

SUMMARY

A disclosed cable includes a roll of flexible substrate. The substrate has opposing first and second surfaces and the roll is structured around an axis. A plurality of electrically conductive wires are attached to the first surface of the substrate, and the roll of flexible substrate and attached plurality of wires have alternating layers of wires and substrate.

The above summary is not intended to describe each disclosed embodiment. The figures and detailed description that follow provide additional example embodiments.

BRIEF DESCRIPTION OF THE DRAWINGS

Other aspects and advantages will become apparent upon review of the Detailed Description and upon reference to the drawings in which.

DETAILED DESCRIPTION

In the following description, numerous specific details are set forth to describe specific examples presented herein. It should be apparent, however, to one skilled in the art, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element. Terms such as over, under, top, bottom, above, below, may be used herein to refer to relative positions of elements as shown in the figures. It should be understood that the terminology is used for notational convenience only and that in actual use the disclosed structures may be oriented different from the orientation shown in the figures. Thus, the terms should not be construed in a limiting manner.

Further challenges faced by the catheter designer are those associated with manufacturability. For example, in order for the resulting product to be cost effective the designer must consider the speed at which the catheter tube can be manufactured, the cost of materials, and the complexity of the manufacturing process. In addition, the desired durability and size of the resulting product will affect the manufacturability, reliability, and durability. Thus, every characteristic of the tube can be critical for the catheter to operate in the desired application.

The disclosed cable provides a number of benefits over conventional approaches for making catheter tubes or other applications that would benefit from small diameter cables. The disclosed cable, which can be a subassembly for a catheter tube or neuro-implant, for example, is thinner and more reliable, durable, environmentally friendly, and economical when compared to prior approaches. The disclosed cable is a rolled substrate having alternating layers of substrate and strands of wire. The strands of wire can be oriented in congruent helixes about an axis of the rolled substrate. Alternatively, the strands of wire can be oriented parallel to the axis of the rolled substrate. In one implementation, the substrate is a layer of adhesive, a layer of adhesive on a carrier film, or two layers of adhesive on a carrier film. Elimination of the traditional substrates used in printed-and-etched structures can result in a cable having a much smaller diameter. In another implementation, the substrate is a flexible substrate and can be one of a polyethylene terephthalate (PET), a polyelectrolyte multilayers (PEMs), paper, a high-density polyethylene, or a vinyl, for example.

Rather than using expensive print-and-etch techniques for the signal-carrying conductors, strands of wire can be adhered to the substrate by a pressure-sensitive adhesive.

Each wire is a fine gauge, round (round cross-section), bare or jacketed wire. For example, 44 gauge (AWG) or equivalent copper, silver-coated copper, or aluminum wire has been found to be suitable for some applications, though the gauge and material may be different for other applications. "Wire" as used herein does not refer to printed or printed-and-etched patterns of conductive material. Rather, as used herein, wire refers to one or more strands of conductive material that have been made, for example, by drawing the conductive material through draw plates, such that the wire has a round cross section. Using a fine gauge copper wire eliminates the use of environmentally hazardous chemicals or expensive lasers as would be required for printing and etching.

The aforementioned types of substrate and wires are applicable to all of the exemplary structures shown in the following figures unless otherwise stated or excluded by implication.

Figure 1:
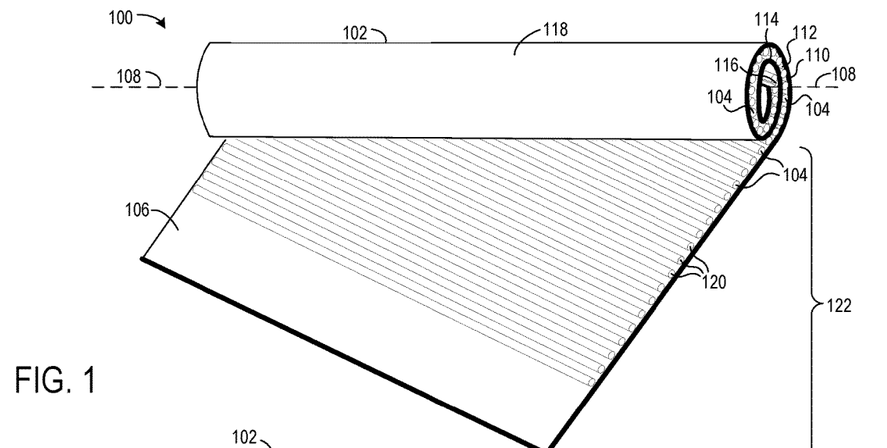
FIG. 1 shows a perspective view of a partially rolled exemplary cable.

FIG. 1 shows a perspective view of a partially rolled exemplary cable. The cable 100 is a roll of flexible substrate 102 having electrically conductive wires, exemplary ones of which are shown as elements 104, attached to surface 106. The cable is partially rolled in that not all of the substrate has been rolled to complete the cable. That is, portion 122 of the substrate remains to be rolled. The substrate and wires are rolled about an axis 108. The wires are oriented in congruent helixes about the axis. The cable has alternating layers of wires and substrate, shown as layers 110, 112, 114, and 116. In the exemplary cable 100, the wires are rolled to the inside of the flexible substrate. That is, the wires are disposed on surface 106, and surface 106 faces toward the axis 108 such that the first surface of the substrate forms an inner surface of the roll, and the wires are disposed on the inner surface of the roll. Opposing surface 118 forms an outer surface of the roll. In some implementations, optic fibers can be disposed on the surface 106 of the substrate 102 along with the wires 104. For example, elements 120 can be optic fibers.

Figure 2:
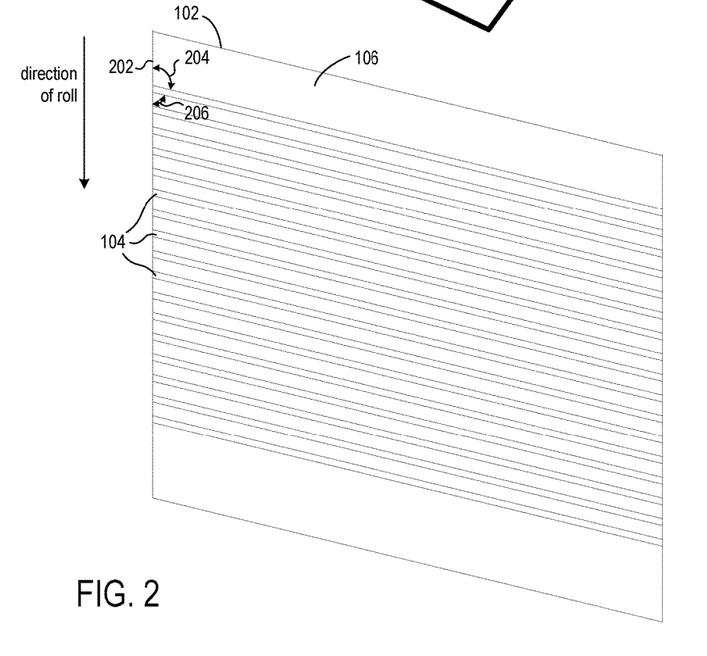
FIG. 2 shows a top view of a substrate having conductive wires attached to surface.

FIG. 2 shows a top view of a substrate 102 having conductive wires 104 attached to surface 106. The structure of FIG. 2 is the state of the substrate and wires prior to being formed into a rolled substrate, such as shown by the cable 100 in FIG. 1. The top view shows the non-rectangular shape of the substrate and orientation of the wires on the substrate.

The wires 104 are parallel to one another on the substrate and are oriented such that the angle formed by the wire and the edge 202 of the substrate is not perpendicular: angle 204 is oblique and angle 206 is acute. Rolling the substrate in a direction parallel to edge 202 produces a structure having wires oriented in congruent helixes and disposed on the inside surface of the rolled substrate such as shown in FIG. 1.

Figures 3, 4:
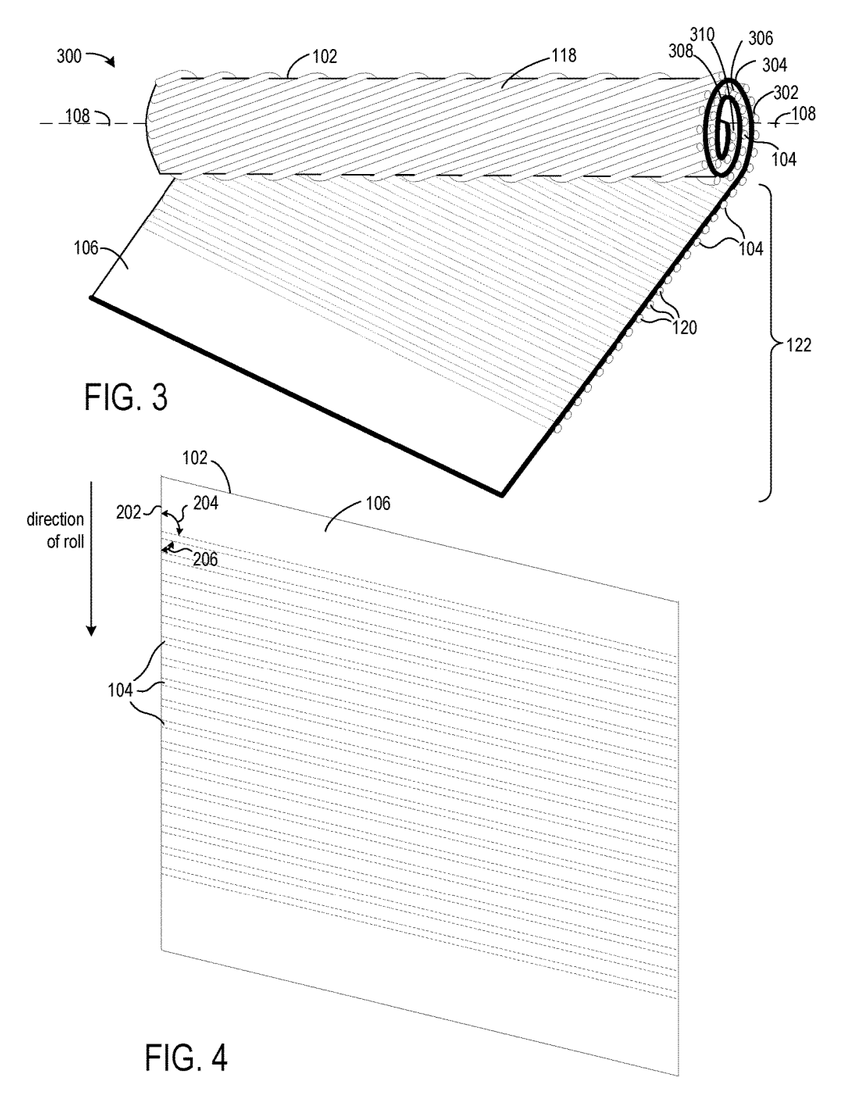
FIG. 3 shows a perspective view of another partially rolled exemplary cable.
FIG. 4 shows a top view of a substrate having conductive wires attached to the surface opposite surface.

FIG. 3 shows a perspective view of a partially rolled exemplary cable. The cable 300 is a roll of flexible substrate 102 having electrically conductive wires, exemplary ones of which are shown as elements 104, attached to surface 118. The cable is partially completed in that not all of the substrate has been rolled to complete the cable. That is, portion 122 of the substrate remains to be rolled. The substrate and wires are rolled about an axis 108. The wires are oriented in congruent helixes about the axis. The cable has alternating layers of wires and substrate, shown as layers 302, 304, 306, 308, and 310. In the exemplary cable 300, the wires are rolled to the outside of the flexible substrate. That is, the wires are disposed on surface 118, and surface 118 faces away from the axis 108 such that surface 118 of the substrate forms an outer surface of the roll, and the wires are disposed on the outside surface of the roll. Surface 106 forms the inner surface of the roll. In some implementations, optic fibers can be disposed on the surface 118 of the substrate 102 along with the wires 104. For example, elements 120 can be optic fibers.

FIG. 4 shows a top view of a substrate 102 having conductive wires 104 attached to the surface opposite surface 106. The dashed lines represent the wires as obscured by the substrate. The structure of FIG. 4 is the state of the substrate and wires prior to being formed into a rolled substrate, such as shown by the cable 300 in FIG. 3. The top view shows the non-rectangular shape of the substrate and orientation of the wires on the substrate.

The wires 104 are parallel to one another on the substrate and are oriented such that the angle formed by the wire and the edge 202 of the substrate is not perpendicular: angle 204 is oblique and angle 206 is acute. Rolling the substrate in a direction parallel to edge 202 produces a structure having wires oriented in congruent helixes and disposed on the inside surface of the rolled substrate such as shown in FIG. 3.

Figure 5:
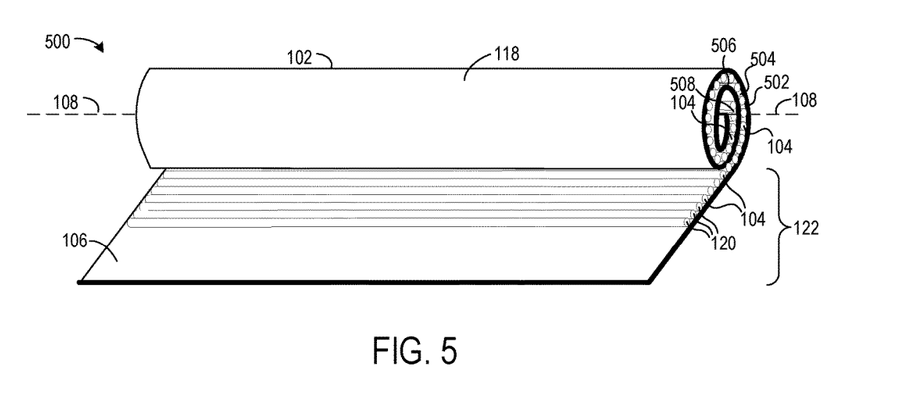
FIG. 5 shows a perspective view of a partially rolled exemplary cable.

FIG. 5 shows a perspective view of a partially rolled exemplary cable. The cable 500 is a roll of flexible substrate 102 having electrically conductive wires, exemplary ones of which are shown as elements 104, attached to surface 106. The cable is partially rolled in that not all of the substrate has been rolled to complete the cable. That is, portion 122 of the substrate remains to be rolled. The substrate and wires are rolled about an axis 108. The wires are oriented parallel to the axis. The cable has alternating layers of wires and substrate, shown as layers 502, 504, 506, and 508. In the exemplary cable 100, the wires are rolled to the inside of the flexible substrate. That is, the wires are disposed on surface 106, and surface 106 faces toward the axis 108 such that the first surface of the substrate forms an inner surface of the roll, and the wires are disposed on the inner surface of the roll. Opposing surface 118 forms an outer surface of the roll. In some implementations, optic fibers can be disposed on the surface 106 of the substrate 102 along with the wires 104. For example, elements 120 can be optic fibers.

Figure 6:
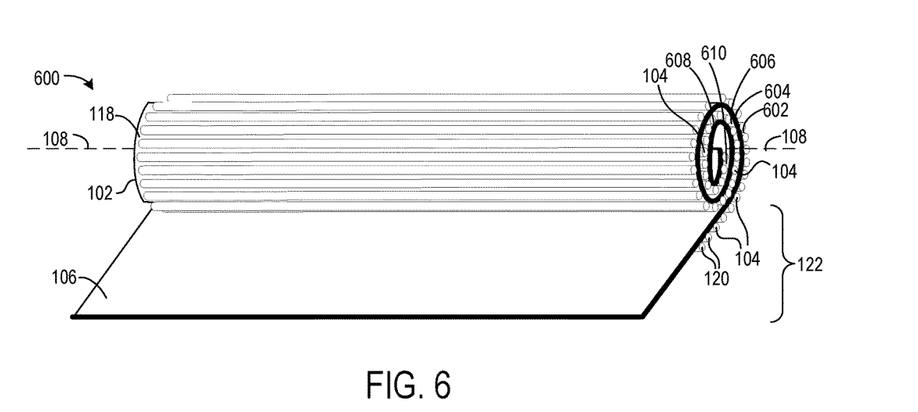
FIG. 6 shows a perspective view of another partially rolled exemplary cable.

FIG. 6 shows a perspective view of a partially rolled exemplary cable. The cable 600 is a roll of flexible substrate 102 having electrically conductive wires, exemplary ones of which are shown as elements 104, attached to surface 118. The cable is partially rolled in that not all of the substrate has been rolled to complete the cable. That is, portion 122 of the substrate remains to be rolled. The substrate and wires are rolled about an axis 108. The wires are oriented parallel to the axis. The cable has alternating layers of wires and substrate, shown as layers 602, 604, 606, 608, and 610. In the exemplary cable 600, the wires are rolled to the outside of the flexible substrate. That is, the wires are disposed on surface 118, and surface 118 faces away from the axis 108 such that surface 118 of the substrate forms an outer surface of the roll, and the wires are disposed on the outer surface of the roll. Opposing surface 106 forms an inner surface of the roll. In some implementations, optic fibers can be disposed on the surface 118 of the substrate 102 along with the wires 104. For example, elements 120 can be optic fibers.

FIGS. 7, 8, 9, 10 and 11 show cross-section views of cables 100 and 500 in FIGS. 1 and 5 having wires rolled on the inside surface of the substrate according to different implementations. Though the views illustrate wires rolled on the inside surface of the substrate, those skilled in the art will recognize that the cables 300 and 600 of FIGS. 3 and 6 can have comparable cross-sections having wires on the outer surface of the substrate instead of on the inner surface of the substrate.

Figure 7:
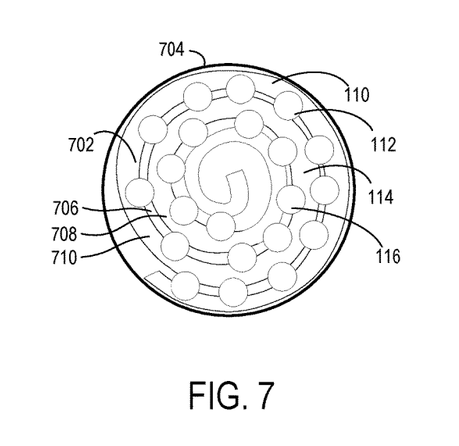
FIG. 7 shows a cross-sectional view of an exemplary cable having an adhesive-only substrate.

FIG. 7 shows a cross-sectional view of exemplary cables 100 and 500. The cross-section shows the alternating layers of substrate and wires, for example, layers 110, 112, 114, and 116. Each wire has a round cross section and can be a jacketed wire or a bare wire. The substrate 702 is a layer of pressure-sensitive adhesive that is unsupported by a carrier film or more rigid material. Spaces between adjacent inner portions and outer portions of the rolled substrate are shown for purposes of illustration only. For example, space 706 is between inner portion 708 and adjacent outer portion 710. It will be recognized that the spaces may not be present in a final structure as one surface of the adhesive layer would adhere to the opposing surface of the adhesive layer as a result of rolling the adhesive layers and wires into a cable.

The cable can further include a jacket 704 that encases the layers of substrate and wires. Depending on implementation restrictions, the jacket can be a separate element attached to the rolled adhesive substrate as shown. The jacket can be any material suitable for the intended application. The space between the jacket and the adhesive layer is shown for purposes of illustration only and would not be present in the completed structure.

Figure 8:
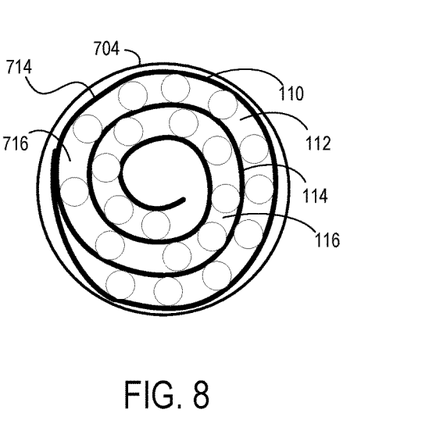
FIG. 8 shows a cross-sectional view of another exemplary cable.

FIG. 8 shows a cross-sectional view of exemplary cables 100 and 500. The cross-section shows the alternating layers of substrate and wires, for example, layers 110, 112, 114, and 116. Each wire has a round cross section and can be a jacketed wire or a bare wire. The wires can be attached to the substrate 714 by a pressure-sensitive adhesive (not shown), for example, and the adhesive can fill the wire layers in spaces between the wires. For example, space 716 can be filled with adhesive. The substrate 714 can be a material such as PET, PEMs, paper, high-density polyethylene, or a vinyl, for example.

Figure 9:
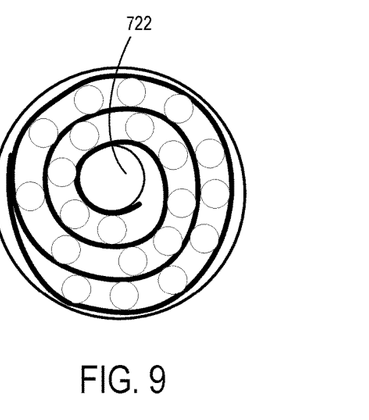
FIG. 9 shows an implementation of a cable having a single flexible core.
Figure 10:
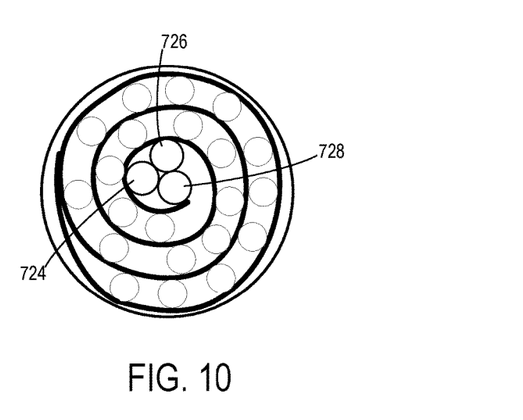
FIG. 10 shows an implementation of a cable having multiple flexible cores.

FIGS. 9 and 10 show flexible cores at the center of the cross-sectional views of the cables. FIG. 9 shows an implementation having a single flexible core 722, and FIG. 10 shows an implementation having multiple flexible cores 724, 726, and 728. The flexible cores can be optic fibers, for example, or some other material if signal carrying is not required. The cores are oriented parallel to the axis of the cable.

Figure 11:
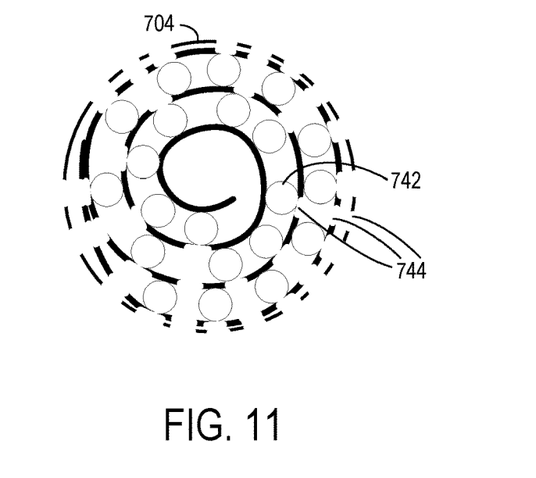
FIG. 11 shows openings in the substrate that allow for connections to the wires of the cable.

FIG. 11 shows openings in the substrate that allow for connections to the wires of the cable. The exemplary cable includes jacket 704. Access to the wires of the cable can be provided through openings in the jacket and through the several layers of rolled substrate. For example, wire 742 can be accessed through openings 744. The cables of FIGS. 9, 10, and 11 can have adhesive layer-only substrate 702, such as shown in FIG. 7, or have more rigid substrate 714, such as that shown in FIG. 8.

Figure 12:
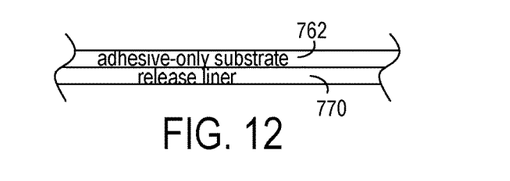
FIG. 12 shows a structure in which a layer of adhesive is by itself the substrate that supports the wire and to which the wires are directly attached.
Figure 13:
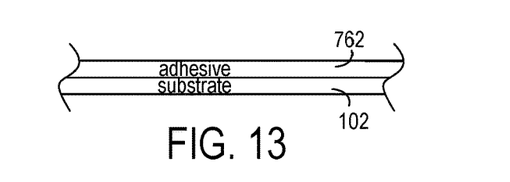
FIG. 13 shows a substrate and a single layer of adhesive.
Figure 14:
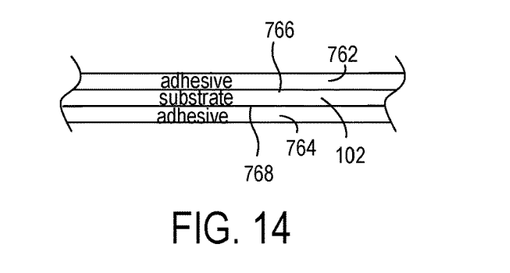
FIG. 14 shows a substrate and adhesive disposed on opposing surfaces of the substrate.

FIGS. 12, 13, and 14 show structures that may be suitable for building the disclosed rolled substrate cables. FIG. 12 shows a structure in which a layer of adhesive 762 is by itself the substrate that supports the wire and to which the wires are directly attached. While wires are in the process of being attached to the layer of adhesive and prior to rolling the adhesive substrate, a release liner 770 is attached to the surface of the layer of adhesive that is opposite the surface on which the wires are being attached. Once the wires are attached, the layer of adhesive can be rolled, and as the adhesive layer is rolled the release liner can be removed. A jacket can be attached to the layer of adhesive after the layer of adhesive and wires have been rolled into a bundle.

FIG. 13 shows a substrate 102 and a single layer of adhesive 762. The adhesive can be a pressure-sensitive adhesive disposed on one surface of the substrate, and the wires (not shown) can be directly attached to the layer of adhesive.

FIG. 14 shows a substrate 102 and adhesive disposed on opposing surfaces of the substrate. Layer 762 of adhesive is disposed on surface 766, and layer 764 of adhesive is disposed on surface 768. Both layers of adhesive can be pressure-sensitive.

The present invention is thought to be applicable to a variety of applications. Other aspects and embodiments will be apparent to those skilled in the art from consideration of the specification and practice of the circuits and methods disclosed herein. It is intended that the specification and illustrated embodiments be considered as examples only, with a true scope of the invention being indicated by the following claims.

What is claimed is:

1. A cable, comprising:
    a roll of flexible substrate, the substrate having opposing first and second surfaces and the roll structured around an axis;
    a plurality of electrically conductive wires attached to the first surface of the substrate, wherein the wires are directly attached to the first surface of the substrate, and the first surface of the substrate faces toward the axis, the first surface of the substrate being an inner surface of the roll, and the plurality of wires are disposed on the inner surface of the roll; and
    wherein the roll of flexible substrate and attached plurality of wires have alternating layers of wires and substrate.

2. The cable of claim 1, wherein the plurality of electrically conductive wires are attached to the first surface of the substrate and are oriented in congruent helixes about the axis.

3. The cable of claim 1, wherein the plurality of electrically conductive wires are attached to the first surface of the substrate and are oriented parallel to the axis.

4. The cable of claim 1, further comprising a flexible core, wherein the roll of flexible substrate is rolled around the flexible core.

5. The cable of claim 1, further comprising an optic fiber, wherein the roll of flexible substrate is rolled around the optic fiber, and the optic fiber forms the axis.

6. The cable of claim 1, further comprising a plurality of optic fibers, wherein the roll of flexible substrate is rolled around the plurality of optic fibers oriented parallel to the axis.

7. The cable of claim 1, further comprising one or more optic fibers attached to the first surface of the substrate and oriented parallel to the axis.

8. The cable of claim 1, further comprising one or more optic fibers attached to the first surface of the substrate and oriented in congruent helixes about the axis.

9. A cable, comprising:
    a roll of flexible substrate, the substrate having opposing first and second surfaces and the roll structured around an axis;
    a plurality of electrically conductive wires attached to the first surface of the substrate; and
    wherein the roll of flexible substrate and attached plurality of wires have alternating layers of wires and substrate, and each wire of the plurality of wires has a round cross section.

10. The cable of claim 1, further comprising a layer of adhesive directly disposed on the first surface of the substrate, wherein the plurality of electrically conductive wires are directly attached to the layer of adhesive.

11. The cable of claim 1, further comprising a first layer of adhesive directly disposed on the first surface of the substrate and a second layer of adhesive directly disposed on the second surface of the substrate, wherein the plurality of electrically conductive wires are directly attached to the first layer of adhesive.

12. The cable of claim 1, wherein:
the roll of flexible substrate is a layer of adhesive; and
the cable further comprises a jacket encasing the roll of flexible substrate.

13. The cable of claim 1, wherein the plurality of electrically conductive wires have round cross sections and each of the wires is comprised of one of copper or aluminum.

14. The cable of claim 1, wherein the plurality of electrically conductive wires are jacketed and have round cross sections.

15. The cable of claim 1, wherein the plurality of electrically conductive wires are bare wires and have round cross sections.

16. A cable, comprising:
a roll of flexible substrate, the substrate having opposing first and second surfaces and the roll structured around an axis;
a plurality of electrically conductive wires attached to the first surface of the substrate;
a jacket, wherein the rolled substrate is encased in the jacket, and the jacket and substrate have openings that expose the plurality of wires for connection; and
wherein the roll of flexible substrate and attached plurality of wires have alternating layers of wires and substrate.

17. The cable of claim 1, wherein each wire of the plurality of wires has a round cross section.

18. The cable of claim 1, further comprising a jacket, wherein the rolled substrate is encased in the jacket, and the jacket and substrate have openings that expose the plurality of wires for connection.

19. The cable of claim 9, wherein the plurality of electrically conductive wires are attached to the first surface of the substrate and are oriented in congruent helixes about the axis.

20. The cable of claim 9, wherein the plurality of electrically conductive wires are attached to the first surface of the substrate and are oriented parallel to the axis.

21. The cable of claim 9, further comprising a flexible core, wherein the roll of flexible substrate is rolled around the flexible core.

22. The cable of claim 9, further comprising an optic fiber, wherein the roll of flexible substrate is rolled around the optic fiber, and the optic fiber forms the axis.

23. The cable of claim 9, further comprising a plurality of optic fibers, wherein the roll of flexible substrate is rolled around the plurality of optic fibers oriented parallel to the axis.

24. The cable of claim 9, wherein the wires are directly attached to the first surface of the substrate, and the first surface of the substrate faces away from the axis, the first surface of the substrate being an outer surface of the roll, and the plurality of wires are disposed on the outer surface of the roll.

25. The cable of claim 9, further comprising one or more optic fibers attached to the first surface of the substrate and oriented parallel to the axis.

26. The cable of claim 9, further comprising one or more optic fibers attached to the first surface of the substrate and oriented in congruent helixes about the axis.

27. The cable of claim 9, further comprising a layer of adhesive directly disposed on the first surface of the substrate, wherein the plurality of electrically conductive wires are directly attached to the layer of adhesive.

28. The cable of claim 9, further comprising a first layer of adhesive directly disposed on the first surface of the substrate and a second layer of adhesive directly disposed on the second surface of the substrate, wherein the plurality of electrically conductive wires are directly attached to the first layer of adhesive.

29. The cable of claim 9, wherein:
the roll of flexible substrate is a layer of adhesive; and
the cable further comprises a jacket encasing the roll of flexible substrate.

30. The cable of claim 9, wherein and each of the wires is comprised of one of copper or aluminum.

31. The cable of claim 9, wherein the plurality of electrically conductive wires are jacketed.

32. The cable of claim 9, wherein the plurality of electrically conductive wires are bare wires.

33. The cable of claim 9, further comprising a jacket, wherein the rolled substrate is encased in the jacket, and the jacket and substrate have openings that expose the plurality of wires for connection.

34. The cable of claim 16, wherein the plurality of electrically conductive wires are attached to the first surface of the substrate and are oriented in congruent helixes about the axis.

35. The cable of claim 16, wherein the plurality of electrically conductive wires are attached to the first surface of the substrate and are oriented parallel to the axis.

36. The cable of claim 16, further comprising a flexible core, wherein the roll of flexible substrate is rolled around the flexible core.

37. The cable of claim 16, further comprising an optic fiber, wherein the roll of flexible substrate is rolled around the optic fiber, and the optic fiber forms the axis.

38. The cable of claim 16, further comprising a plurality of optic fibers, wherein the roll of flexible substrate is rolled around the plurality of optic fibers oriented parallel to the axis.

39. The cable of claim 16, wherein the wires are directly attached to the first surface of the substrate, and the first surface of the substrate faces away from the axis, the first surface of the substrate being an outer surface of the roll, and the plurality of wires are disposed on the outer surface of the roll.

40. The cable of claim 16, further comprising one or more optic fibers attached to the first surface of the substrate and oriented parallel to the axis.

41. The cable of claim 16, further comprising one or more optic fibers attached to the first surface of the substrate and oriented in congruent helixes about the axis.

42. The cable of claim 16, further comprising a layer of adhesive directly disposed on the first surface of the substrate, wherein the plurality of electrically conductive wires are directly attached to the layer of adhesive.

43. The cable of claim 16, further comprising a first layer of adhesive directly disposed on the first surface of the substrate and a second layer of adhesive directly disposed on the second surface of the substrate, wherein the plurality of electrically conductive wires are directly attached to the first layer of adhesive.

44. The cable of claim 16, wherein the roll of flexible substrate is a layer of adhesive.

45. The cable of claim 16, wherein and each of the wires is comprised of one of copper or aluminum.

46. The cable of claim 16, wherein the plurality of electrically conductive wires are jacketed.

47. The cable of claim 16, wherein the plurality of electrically conductive wires are bare wires.

\* \* \* \* \*